(12) United States Patent
Salafsky et al.

(10) Patent No.: US 6,447,801 B1
(45) Date of Patent: Sep. 10, 2002

(54) ANTI-PARASITIC ACTION OF N,N-DIETHYL-M-TOLUAMIDE (DEET) AND FORMULATIONS THAT PROLONG ITS ACTIVITY IN THE SKIN

(76) Inventors: Bernard Salafsky, 5730 Clarendon Dr., Rockford, IL (US) 61114; Ramaswamy Kalyanasundaram, 1423 Illini Dr., Rockford, IL (US) 61107; Takeshi Shibuya, 2-14-19 Kamiohsaki, Shinagawa-Ku, Tokyo (JP), 141

( * ) Notice: Subject to any disclaimer, the term of this patent is extended or adjusted under 35 U.S.C. 154(b) by 0 days.

(21) Appl. No.: 09/283,883

(22) Filed: Apr. 1, 1999

Related U.S. Application Data (63) Continuation-in-part of application No. PCT/US98/02398, filed on Feb. 10, 1998.
(60) Provisional application No. 60/040,251, filed on Feb. 11, 1997.

(51) Int. Cl.[7] .......................... A01N 25/28; A61K 9/127
(52) U.S. Cl. ........................ 424/450; 424/405; 424/406; 424/408; 424/DIG. 10; 514/617; 514/875; 514/919
(58) Field of Search ................ 424/405–408, 424/417, 420, 450, 489–490, 498, 502, DIG. 8, DIG. 10; 514/617, 829, 830, 875, 895, 947, 963, 330, 551, 729, 456, 876, 919

(56) References Cited

U.S. PATENT DOCUMENTS

| | | | |
|---|---|---|---|
| 4,241,046 A | * 12/1980 | Papahadjopoulos et al. | 424/450 |
| 4,855,090 A | * 8/1989 | Wallach | 264/4.1 |
| 4,869,896 A | * 9/1989 | Coulston et al. | 424/45 |
| 5,019,392 A | * 5/1991 | Wallach | 424/450 |
| 5,145,604 A | * 9/1992 | Neumiller | 252/312 |
| 5,173,303 A | 12/1992 | Lau et al. | 424/450 |
| 5,221,535 A | 6/1993 | Domb | 424/450 |
| 5,788,975 A | * 8/1998 | Laversanne et al. | 424/417 |

FOREIGN PATENT DOCUMENTS

JP        06183910    * 7/1994

OTHER PUBLICATIONS

M.B. Abou–Donia, K.R. Wilmarth, "Neurotoxicity Resulting From Coexposure To Pyridostigmine Bromide, DEET, And Permethrin: Implications Of Gulf War Chemical Exposures", *J. Toxicol. Environ. Health*, 48:35–56 (1996).

R.R. Abu–Elyazeed, J.K. Podgore, N.S. Mansour, M.E. Kilpatrick, "Field Trial Of 1% Niclosamide As A Topical Antipenetrant To *Schistosoma mansoni* Cercariae", *Am. J. Trop. Med. Hyg.*, 49(4):403–409 (1993).

M. Bar–Zeev, S. Gothilf, "Laboratory Evaluation Of Flea Repellents", *J. Med. Ent.*, 9(3):215–218 (1972).

P. Couch, C.E. Johnson, "Prevention Of Lyme Disease", *AJHP*, 49:1164–1173 (1992).

J.T. DiPiro, R.L. Talbert, P.E. Hayes, G.C. Yee, L.M. Posey, in Pharmacotherapy: A Pathophysiologic Approach, New York: Elsevier Science, pp. 1196–1198 and 1204–1205 (1989).

(List continued on next page.)

*Primary Examiner*—Neil S. Levy
(74) *Attorney, Agent, or Firm*—Woodard, Emhardt, Naughton, Moriarty & McNett (57) ABSTRACT

Novel formulations of DEET are provided which comprise liposomes and other carriers. Methods and materials for preventing Schistomiasis and other parasitic and microbial diseases are also provided. Also provided are improved materials and methods for repelling biting insects.

35 Claims, 2 Drawing Sheets

LONG TERM EFFECT OF DEET APPLICATION

OTHER PUBLICATIONS

D.C. Dorman, "Diethyltoluamide (DEET) Insect Repellent Toxicosis", *Veterinary Clinics of North America: Small Animal Practice*, 20:387–391 (1990).

P.M. Elias, "Lipids And The Epidermal Permeability Barrier", *Arch. Dermatol. Res.*, 270:95–117 (1981).

P.J. Fripp, F.I. Armstrong, "The Efficacy Of A Hexachlorophene Skin Cleanser As A Cercaria Repellent", *South African Medical Journal*, 47:526–527 (1973).

A.M. Ghandour, G. Webbe, "The Effect of Sublethal Concentrations Of The Molluscicide Niclosamide On The Infectivity Of *Schistosoma mansoni* Cercariae", *J. Helminthology*, 49:245–250 (1975).

M.M. Grenan, L.K. Greene, D.E. Davidson, Jr., D.H. Jones, T.R. Shedd, G. Hiestand, "Hexachlorophene As A Topically Applied Chemical For Prophylaxis Against *Schistosoma mansoni* Infections In Mice", *Rev. Inst. Med. Trop. Sao Paulo*, 27(4):190–196 (1985).

Y. He, C. Mao, Y. Hu, "Comparison Of Some Physiology Aspects Between Cercariae And Newly Transformed Schistosomula Of *Schistosoma japonicum*", *Acta Zoologica Sinica*, 31(3):240–245 (1985) (See English language abstract).

S. Kumar, S. Prakash, M.P. Kaushik, K.M. Rao, "Comparative Activity Of Three Repellents Against The Ticks *Rhipicephalus sanguineus* And *Argas persicus*", *Medical and Veterinary Entomology*, 6:47–50 (1992).

J–W. Li, K. Ramaswamy, B. Salafsky, Y–X. He, T. Shibuya, "Tran$^{35}$S–Labeling Of Cercariae Of *Schistosoma mansoni*: A Less Expensive Tool For Tracing In Vivo Migration Of Schistosomula In Mice", *Parasitology International*, 46:55–65 (1977).

Z.A. Mehr, L.C. Rutledge, J.L. Inase, "Evaulation Of Commercial And Experimental Repellents Against *Xenopsylla cheopis* (Siphonaptera: Pulicidae)", *J. Med. Entomol.*, 21(6):665–669 (1984).

J.M. Naples, C.J. Shiff, K–H.A. Rosler, "*Schistosoma mansoni*: Cercaricidal Effects Of Cedarwood Oil And Various Of Its Components", *Journal of Tropical Medicine and Hygiene*, 95:390–396 (1992).

B. Salafsky, A.C. Fusco, K. Whitley, D. Nowicki, B. Ellenberger, "*Schistosoma mansoni*: Analysis Of Cercarial Transformation Methods", *Experimental Parasitology*, 67:116–127 (1988).

B. Salafsky, K. Ramaswamy, Y–X. He, G.L. Anderson, D.K. Nowicki, T. Shibuya, "Evaluation Of N,N–Diethyl–m–Toluamide (DEET) As A Topical Agent For Preventing Skin Penetration By Cercariae Of *Schistosoma mansoni*", *Am. J. Trop. Med. Hyg.*, 58(6):828–834 (1998).

S. Selim, R.E. Hartnagel, Jr., T.G. Osimitz, K.L. Gabriel, G.P. Schoenig, "Absorption, Metabolism, And Excretion Of N,N–Diethyl–m–Toluamide Following Dermal Application To Human Volunteers", *Fundamental and Applied Toxicology*, 25:95–100 (1995).

V.B. Solberg, T.A. Klein, K.R. McPherson, B.A. Bradford, J.R. Burge, R.A. Wirtz, "Field Evaluation Of Deet And A Piperidine Repellent (AI3–37220) Against *Amblyomma Americanum* (Acari: Ixodidae)", *J. Med. Entomol.*, 32(6):870–875 (1995).

J.C. Veltri, T.G. Osimitz, D.C. Bradford, B.C. Page, "Retrospective Analysis Of Calls To Poison Control Centers Resulting From Exposure To The Insect Repellent N,N–Diethyl–m–Toluamide (DEET) From 1985–1989", *Clinical Toxicology*, 32(1):1–16 (1994).

R.D. Verschoyle, A.W. Brown, C. Nolan, D.E. Ray, T. Lister, "A Comparison Of The Acute Toxicity, Neuropathology, And Electrophysiology Of N,N–Diethyl–m–Toluamide And N,N–Dimethyl–2,2–Diphenylacetamide In Rats", *Fundamental and Applied Toxicology*, 18:79–88 (1992).

J.C. Wang, "Delivery Systems Of Cosmetic Ingredients: Technology, Trends, And Market Oppportunities", *Drug and Market Development*, 8:166 (1997).

Who Expert Committee On The Control Of Schistosomiasis, "Public Health Impact Of Schistosomiasis: Disease And Mortality", *Bulletin of the World Health Organization*, 71(6):657–662 (1993).

USCDI THIABENAZOLE p. 2309, 1989.*

* cited by examiner

ANTI-PARASITIC ACTION OF N,N-DIETHYL-M-TOLUAMIDE (DEET) AND FORMULATIONS THAT PROLONG ITS ACTIVITY IN THE SKIN

CROSS REFERENCE TO RELATED APPLICATIONS

This application is a Continuation-In-Part of PCT Application No.: US98/02398 filed Feb. 10, 1998, which claims priority from U.S. Provisional Application No. 60/040,251, filed Feb. 11, 1997.

BACKGROUND OF THE INVENTION

Parasites and microbial organisms that gain entry into human and animal hosts by (a) penetrating through the skin or (b) being "delivered" via other vectors (e.g., mosquitoes, ticks, flies, etc.) through the skin, are responsible for a very large proportion of disease. An example of an organism penetrating the skin is schistosomiasis, which is a life threatening infection of humans and animals in many tropical and subtropical parts of the world. According to the World Health Organization (WHO) estimate there are currently over 200 million people infected with this parasite and another 600 million at risk. [WHO Expert Committee on the Control of Schistosomiasis: Public Health Impact of Schistosomiasis Disease and Mortality Bulletin of the World Health Organization, 71:657–662, 1993]. Travelers visiting such endemic areas are at greater risk of acquiring the disease and disseminating it further. Skin is the only known route of entry for this parasite into humans and animals with the infective stage (cercariae) of the parasite having the ability to penetrate intact skin within a matter of minutes after water contact. Therefore, any agent that will interfere with entry of cercaria into the skin will essentially prevent schistosomiasis. Another disease condition called "swimmers itch" or "cercarial dermatitis" is caused by inadvertent entry of the cercariae of animal schistosomes (i.e. *Trichobilharzia ocellata*) into human skin resulting in severe dermatitis. This condition is widely prevalent in the many fresh water lakes of the United States, Asia, and New Zealand as well as the rice paddies of Asia. Similarly, hookworm parasites, particularly *Necator americanus*, directly infect man and animals by penetrating intact skin. The mature worm lives in the stomach, daily consuming a blood meal and contributing to the malnourishment of the host. Further, infection with this parasite is often attended with other disease states. It is conservatively estimated that approximately one billion people may be infected with hookworm.

Arthropods and related species "deliver" parasites and other microbial disease-producing organisms through the skin after biting the host. Best known and most problematic is malaria, which effects millions of people in tropical and subtropical regions of the world. According to WHO estimates, malaria ranks among the top five leading causes of death worldwide. Over the past 20 years the malaria problem has been exacerbated by the appearance of drug resistant strains. Mosquitoes are also known to be carriers of non-parasitic diseases such as Dengue, Yellow Fever, and other conditions. Various species of ticks are responsible for Lyme Disease, Rocky Mountain Spotted Fever, Ehrlichiosis, Colorado Tick Fever, Tularemia, Relapsing Fever, Powassan Encephalitis and tick paralysis.

According to the Centers for Disease Control and Prevention (CDC) more cases of tick borne disease were reported during the 1994–1997 period than the combined total of cases reported for measles, mumps, whooping cough, rubella, diphtheria, cholera, leptospirosis, leprosy, plague, tetanus, trichinosis, typhoid fever, giardiasis, and Legionnaire's disease in the U.S. Ticks infect humans and animals by taking a blood meal thereby introducing their own infected saliva into the host.

Sand flies will also bite human hosts thereby introducing the organism responsible for human Leishmaniasis. There are many additional examples of arthropods (black flies, gnats, chiggers, deer flies, fleas, tsetse flies, reduviid bugs, etc.) that can cause disease through skin bites.

Independent of disease caused by these arthropods and related species their bites are the cause of significant annoyance and discomfort both in tropical climates and more temperate summer climates. The economic impact of all these diseases and discomfort is significant.

SUMMARY OF THE INVENTION

The invention is directed to materials and methods for preventing parasitic diseases. In particular the invention is directed to preventing parasitic diseases which are caused by skin penetrating parasites or by parasites that are introduced into a host animal via an arthropod vector. The invention is also directed to material and methods for repelling insects.

Exemplary parasitic disease include Schistosomiasis swimmers itch and diseases caused by Ancylostoma species, Necator species, Strongyloides species and others. Exemplary biting insects include ticks, sand flies, black flies, triatomid bugs, reduviid bugs, fleas, mosquitoes, and other species of arthropod vectors that transmit infectious diseases in humans and animals.

Materials useful in the practice of the present invention include N,N-diethyl-m-toluamide (DEET) and formulations of DEET which prolong the effectiveness of DEET and which require lower concentration doses than those commonly used. Such formulation include DEET enveloped in liposomes or in combination with polymers and polyolprepolymers. Liposomes/DEET formulations according to the present invention do not require the presence of an "environment enhancing" chemical like pyridinethione (ZPT) as a skin anchoring chemical moiety for increasing their effectiveness. The formulations described above are also useful for repelling biting insects.

Liposomes may be anionic, cationic or neutral. Preferred liposomes are cationic liposomes comprising L-α-phosphatidylcholine, stearylamine and cholesterol. Preferred concentrations of DEET include from about 1% to about 50% w/v. More preferred are concentrations from about 7% to about 10%. Most preferred is a concentration of about 7.5% DEET. Preferred polyolprepolymers of the invention include polyolprepolymer 2 and polyolprepolymer 15.

The present invention also embodies Liposome/DEET formulations with other insect repellants and ant-parasitic drugs.

DETAILED DESCRIPTION OF THE INVENTION

During the last 30–40 years several chemical compounds were screened by different laboratories for their ability to confer protection against cercarial penetration Among these, a few compounds such as Niclosamide, Cederol, artemether, hexachlorophene, dibutyl phthalate, benzyl benzoate, and many crude preparations from indigenous plants were found to have significant cercaricidal effects in tissue culture. However, except for Niclosamide (Naples, J. M., et al., *J. of Tropical Med. and Hygiene* 95:390–396 1992; Grenan, M. M., et al,. *Rev. Inst. Med. Trop. Sao Paolo* 27: 190–196 (1985); Ghandour, A. M., et al. *J. of Helminthology*, 49: 245–250 (1975); Fripp, P. J., et al., *South African Medical Journal* 47: 526–527 (1974); Abu-Elyazeed, R. R., et al., *Am. J. of Trop. Med. and Hygiene* 49: 403–409 (1993)) none of the other chemicals were tested for their clinical application in humans.

N,N-diethyl-m-toluamide (DEET) is an active ingredient in many insect repellants. Its relative safety and broad spectrum of repellancy (i.e., most mosquitoes strains, ticks, sand flies, etc) have made it an almost ideal product. In addition, chemical research has produced a number of DEET analogs and other related compounds determined by the U.S. Government to have varying degrees of repellancy to insects of different species, for varying lengths of time, with varying safety or other drawbacks. None have consistently enjoyed as widespread use as DEET, although a number of compounds (N-benzoyl piperidine, N-toluyl piperidine, 2-ethoxy benzamide, N-butyl acetanilide, N-ethyl acetanilide, N,N-diethyl-3-methylbenzamide, diethyl phenyl-acetamide, dimethylphthalate, N,N-diethyl-2,5-dimethylbenzamide or DEET isomers such as N,N-diethyl-p-toluamide and 2-ethyl-1,3-hexanediol) have comparable activities as insect repellents against many biting insects of human and animals.

Almost all the studies on DEET to date repeatedly confirm that DEET is a life-saving chemical when used cautiously. Once applied to the skin DEET has an insect repellent activity ranging from 30 minutes to 2 hrs. However, to obtain a longer duration of activity of more than 60 minutes there is a need to apply, often repeatedly, higher concentrations of DEET (as high as 70%). Unfortunately, this may cause occasional neurotoxic symptoms in susceptible individuals and children due to massive absorption of DEET through the skin. (Abou-Donia, M. B. et al., *J of Toxicol and Clinical Toxicol* 32: 1–16 (1996); Veltri J. C., et al., *J. of Toxicol. and Clinical Toxicol*, 32:1–16, (1994); Verschoyle R. D., et al., *Fundamentals of Applied Toxicol* 18: 79–88 (1992); Dorman D. C., *Veterinary Clinics of North America Small Animal Practice* 20: 387–391 (1990)). Therefore, any agent that retards the absorption of DEET through the skin will reduce the toxicity associated with high concentrations of DEET and prolong its repellent activity on the superficial layers of the skin. Furthermore, there is also an added advantages that if DEET is retained on the skin for a longer duration of time, even lower concentration of DEET could be used more effectively, thus reducing any possibility of toxicity associated with absorption.

As described below, the present invention provides a new application for DEET, that of conferring protection against skin penetrating parasites. As demonstrated below, with one application to the skin, DEET was highly effective in preventing the entry of these parasites through the skin and thus protecting the host from the deadly and/or debilitating diseases. The results also demonstrate that the repellent activity of DEET formulations is water resistant. Even after four hours of application, the majority of these water borne parasites were unable to penetrate the skin. Those that did penetrate the DEET applied area were killed within minutes in the skin, potentially helping the host to build up an immune response against the parasite.

Intracellular epidermal lipids are a group of heterogenous polar lipids that confer barrier function to the skin and thus play a major role in regulating skin permeability (Elias P. M., *Archives of Derm. Res.* 270: 95–102 (1981). Because of these lipid barriers, many conventional drugs applied to the skin surface may fail to get to the site of action. For this reason many penetration enhancers were introduced for topical therapy of skin diseases (Santus, et al., *J. Control. Rel. Subst.*, 25:1–27 (1993). However, the majority of these penetration enhancers disturb the intercellular lipid bilayers and thus often exhibit overt toxic or irritant side effects. In this regard several polymers and liposomes proved to be excellent vehicles for transfer of drugs to the superficial layers of the skin.

According to the present invention, two such polymers Pp2, (polyolpolymer 2) Pp15 (polyolpolymer 15) and a lipsome preparation for delivery and retardation of DEET absorption from the superficial layers of the skin were developed. Thus, in order to prolong the activity of DEET in the skin, three new exemplary formulations of 10% DEET (Pp2deet, Pp15deet and Lipodeet) were prepared. When applied to the skin, these preparations conferred protection against skin penetrating parasites for up to 48 hrs after a single application. Pharmacologic and histologic studies using $^{14}$C-labeled DEET suggest that these formulations allow the superficial layers of the skin to retain >90% of the applied DEET during the first 24 hrs after application. Formulations of the present invention were also effective against some biting insects such as ticks and mosquitoes. Given its potent activity against skin penetrating parasites and biting insects for a prolonged period of time (that is over 48 hrs) the long acting DEET formulations of the present invention have a great potential for field control of infectious diseases acquired through the skin.

In the mid 1960's Alec Bagham noted that phospholipids formed closed vesicles in the presence of water and the physicochemical characteristics of these vesicles were similar to a cell membrane. The majority of phospholipids are amphipathic. An amphipathic lipid molecule resembles a lollipop with a round hydrophilic head formed of phospholipid and a long non-polar hydrophobic tail. Several molecules of these amphipathic lipids lined parallel and joined together, by the tail region with heads pointing out, form a lipid bilayer. In a water medium, the bilayer folds up on itself to form a closed sphere that entraps aqueous molecules inside. These vesicles are now called lipsomes. Liposomes are thermodynamically stable and when applied to the skin will fuse with the lipids in the stratum corneum and thus do not penetrate very deeply into skin layers. This will thus minimize systemic absorption of lipsome delivered drugs. The advantages of liposomes are that they are potentially non-toxic, degradable and non-immunogenic. Furthermore, liposomes can store both water-soluble and lipohilic substances due to their amphipathic structure. It is important to note as C. T. Wang (Vice-President of Research and Technology at the Formulation Technology Resource Center, Johnson and Johnson Consumer Products Worldwide, Skillman N.J.) stressed, that there is no universal liposome system to serve all applications (See, "Delivery Systems for Cosmetic Ingredients: Technology Trends and Market Opportunities," P. Bassett, Southborough, Mass. 1997). A special type and structure design of a liposome system is normally required for a selected molecule in order to achieve the maximum benefits of liposomal delivery.

Generally liposomes are prepared with naturally occurring glycerophospholipids such as phosphatidylcholine, cholesterol, stearylamine, phosphatidylserine, and phosphatidylglycerol. When mixed with water (or any water soluble buffer) under low sheer conditions, each molecule of the phospholipids will arrange itself side by side in like orientation (heads up and tails down) to form a sheet. If DEET is added to the phospholipid mixture, being lipid soluble DEET will intersperse uniformly with the phospholipids and form part of the sheet. Two such sheets will then join tail-to-tail to form a bilayer membrane that entraps a small layer of water inside a vesicle. Because of the hydrophobic nature, typically several of these vesicle will form one inside the other in diminishing sizes, creating a multilamellar structure of concentric phospholipids spheres separated by layers of water. These spherical vesicles are termed multilamellar liposome micelles. Since DEET can be incorporated into the micelles, we have coined the term lipodeet for these DEET containing liposomes. For the purpose of this invention lipodeet will refer to any preparation of liposomes that incorporates DEET or its derivatives in any concentration or form. Since lipodeet uses water based buffer to form the micelles, the present invention opens up an array of possible uses that incorporate anti-parasitic drugs into the lipodeet micelle which will effectively prevent many parasitic infections that are acquired through the skin. Since natural phospholipids are used in our lipodeet preparation, toxic effects on the host due to liposomes are minimal.

The electrostatic charge of the phospholipid molecules in the micelle will ultimately decide the final charge of the lipodeet preparation. Thus, phosphatidylcholine and cholesterol that have neutral charges will produce a neutral lipodeet. Whereas addition stearylamine to the preparation will make the lipodeet positively charged. Similarly, addition of phosphatidylserine or phosphatidylglycerol will impart an overall negative charge to the lipodeet preparation. In this invention we have used all three different charges of lipodeet (positive, negative, and neutral) and all these preparation gave comparatively similar results.

Thus, formulations of the present invention also have the added advantage that any number of combination of water-soluble drugs including anthelmintics, antiprotozoans, vaccines etc. can be incorporated into the lipodeet micelle. Furthermore, this invention also expands the application of using DEET in combination with various vehicles including but not limited to agents such as 1-dodecyl azacyloheptan-2-one (laurocparam, Azone), Catzomes, hexamethylene lauramide derivatives, azacycloalkanone derivatives, pyrrolidones, fatty acids, and terpenes, that will retain the DEET in the superficial layers of the skin. Microemulsions comprising DEET are also comprehended by the present invention. Such microemulsions comprise DEET in an oil, water and amphiphile system that is macroscopically monophasic, optically isotropic, thermodynamically stable and is characterized by ultra-low interfacial tension value. When DEET is retained in the superficial layers of the skin, it will have potential repelling action on biting insects and lethal effects on skin penetrating parasites as set out below.

Application of DEET Against Cercarial Stages of Human and Animal Schistosomes As discussed above, skin is the only known route of entry for schistosome parasites into humans and animals. Infective stages of the parasite (cercariae) penetrate intact skin within minutes after water contact. Therefore, any agent that will interfere with entry of cercaria into the skin will essentially prevent schistosomiasis. The following examples demonstrate that DEET is highly lethal for cercariae of *Schistosoma mansoni* and when applied to the skin will prevent entry and establishment of the infection. After a single application, the long acting formulations of DEET, specifically lipodeet will protect the host for up to 48 hrs against penetrations of cercariae and therefore protect against schistosomiasis.

Another disease condition which may, according to the present invention, be prevented using the formulation described herein in human called "swimmers itch" or "cercarial dermatitis" caused by animal schistosomes, can be prevented or treated with DEET. More than a dozen species of dermatitis-causing schistosomes including *Trichobilharzia ocellata, T. physellae, T. stagnicola, T. anatina, T. berghei, T. schoutedeni, T. maegraithi, Giganthobilharziahuttoni, G. gyrauli, G. huronensis, G. sturniae, Austrobilharzia variglandis, A. enneri, Ornithobilharzia canaliculata, O. pricei, Schistsosomatium douthitti* have been described in the Great Lakes region of the United States. Snails that transmit these diseases are widely prevalent in many lakes of North America. The disease is characterized by an intense itch, edema and reddish inflamed areas in the skin that was exposed to the water. Severe infections will lead to insomnia and fever. The reaction becomes intense on repeated contact. Since our invention shows that lipodeet is highly effective against cercarial stages of schistosome, cercarial dermatitis could be prevented by the application of long acting DEET to the skin.

Application Against Other Skin Penetrating Parasites

There are several human and animal nematode parasites such as *Necator americanus*, Ancylostoma sp. and, *Strongyloides stercolaris* that use skin as a port of entry into the body. Although these parasites remain in the skin only for a very short period of time (few minutes), DEET may have a lethal effect on these skin penetrating parasites and thus preventing their migration through the skin. Therefore, the present invention is also directed to the protection of a host animal against many skin penetrating nematode parasites that cause debilitating disease.

Application Against Mosquitoes for Control of Mosquito Borne Disease

Given that the activity of the DEET formulations of the present invention remain in the skin for over 48 hrs, they may be used for repelling activity against mosquitoes of the species Anophilus and Culicine for extended periods of time at a lower concentration as compared to other DEET formulations.

Application Against Ticks and Tick Borne Disease

Tick borne infections are one of the fastest growing infectious disease in North America. Infections that are transmitted by ticks include Lyme disease, Babesiosis, Ehrlichiosis, Rocky Mountain spotted fever, Colorado tick fever, Tularemia, Relapsing fever, Powassan encephalitis, and tick paralysis. These infective agents are transported into the host via tick saliva during their feeding. According to the Centers for Disease Control and Prevention (CDC) more number of tick borne infections were reported during the period of 1994–1997 than the combined total cases reported for measles, mumps, whooping cough, rubella, diphtheria, cholera, malaria, leptospirosis, leprosy, plague, tetanus, trichinosis, typhoid fever, giardiasis, and Legionnaire's disease. Therefore, any agent that can repel or prevent ticks from biting on to the skin will prevent essentially all tick transmitted diseases. DEET is known to be effective against ticks under laboratory conditions (Solberg, V. B., et al., *J. of Med. Entomology* 32: 870–875 (1995); Kumar, S., et al., *Med. Veterinary Entomology* 6:47–50 (1992); Couch P., et al., *American Journal of Hosp. and Pharm.* 49:1164–1173 (1992)). However, application of DEET for control of tick bites under field condition is limited due to its fast clearance from the skin and its short period of activity. It is impractical to apply DEET every 30 min on grazing animals or person hiking through a tick infested vegetation. As set out below, 10% lipodeet when applied to the skin will prevent attachment of ticks for over 72 hours. Ticks that did try to bite the lipodeet applied skin are killed within minutes. Therefore, long acting DEET formulations of the present invention (Lipodeet, Pp2deet, Pp15deet) will be of great benefit under field condition to control tick bites and thus prevent tick transmitted diseases.

Application Against Other Biting Insects Such as Sand Flies, Triatomid Bugs, Fleas, and Black Flies Long acting DEET formulations of the present invention will also be useful in controlling other biting insects such as sand flies that transmit leishmaniasis, triatomid bugs that transmit trypanosomiasis, and black flies that transmit onchocercasis. Since lipodeet remains in the superficial layers of the skin for a longer duration of time, the biting insects will be repelled for a prolonged period of time with one application. In insect prone areas this will also reduce the occasional toxicity associated with repeated application of DEET.

Application Against Leeches and Other Skin Biting Organisms Such as Lice

Since DEET has been shown to be effective against leeches and lice (Mehr Z. A. et al., *J. of Med Entomology* 21:665–669 (1984); Bar-Zeev M., et al., *J. of Med. Entomology* 9:215–218 (1972)), formulations of the present invention may also be used in methods for controlling leech bites and lice infestation.

The following examples are offered for illustrative purposes only, and are not intended to limit the scope of the invention as set out in the appended claims.

Example 1 describes preparation and collection of radio-labeled cercariae.

Example 2 describes the infection of animals with cercariae.

Example 3 describes whole organ auto-radiography.

Example 4 describes the screening of chemical compounds as anti-penetration agents.

Example 5 describes in vitro effect of DEET on *S. mansoni* cercariae.

Example 6 describes the effect of DEET on the morphology of cercariae.

Example 7 describes the in vivo effects.

Example 8 describes the effect of various concentrations of DEET on cercariae penetration and worm establishment.

Example 9 describes the effect of DEET after exposure to infections with *S. mansoni*.

Example 10 describes the duration of activity of DEET after a single skin application.

Example 11 describes preparation of formulations which prolong the effect of DEET.

Example 12 describes s tudies directed to the localization in skin of DEET formulations.

Example 13 describes the effect of DEET formulations on biting insects.

Example 14 describes the effect of long-acting DEET formulation on tick attachment to the skin.

Example 15 describes the effect of Lipodeet on other biting insects.

Example 16 describes results of the studies on the retention of DEET and Lipodeet activity on the skin following exposure to water.

Example 17 compares the efficacy of different concentrations of DEET and Lipodeet against ticks.

Example 18 describes studies comparing the absorption of DEET and Lipodeet through the skin.

Example 19 describes the studies evaluating the efficacy of Lipodeet as a mosquito repellant in humans.

Example 20 describes formulations of DEET and Lipodeet with other congeners.

EXAMPLE 1

Preparation and Collection of Radio-Labeled Cercariae

*Biomphalaria glabrata* species of snails infected with *S. mansoni* were obtained from Dr. Fred Lewis, University of Massachusetts, Lowell, MASS. as part of a sub-contract from National Institute of Allergy and Infectious Diseases (AI # 052590). The infected snails were maintained in continuously aerated chlorine free water in a dark room maintained at a constant temperature of 85–87° F. The water in the snail tank was changed three times a week and the snails were fed with small amounts of autoclave sterilized lettuce and a piece of chalk. Approximately 30 days after the infection date, snails were checked individually for the presence of the parasite by observing the emergence of cercariae from them as a result of exposure to a bright light source for 1 hour. After determining that the snails were releasing cercariae, they were radio-labeled with $^{35}$S-methionine as described previously in Li et al., *Parasitology International*, 46:55–65 (1997). Briefly, snails suspended in distilled water (0.5 ml/snail) were exposed to 20 $\mu$Ci/ml of radiolabelled $^{35}$S-methionine (Tran$^{35}$S-label, ICN Pharmaceuticals, Inc., Irvine, Calif.; specific activity: 1047 Ci/mmol; catalog #51006) at 37° C. in the dark. After 16 hours of exposure to the radioisotope, the snails were rinsed and moved to fresh aerated water and kept in the dark for three days before inducing shedding of the cercariae.

Cercariae were collected by suspending snails in warm distilled water and exposing them to a bright light source for 1 hour. The emerging radio-labeled cercariae were then collected and concentrated by passing through a wire mesh sieve (38 $\mu$m; Newark Wire Cloth Co., Newark, N.J.). After collection the radio-labeled cercariae were suspended in distilled water, counted and used in infection. The procedure consistently yielded >99% radiolabeled cercariae.

EXAMPLE 2

Infection of Laboratory Animals with Schistosome cercariae

For in vivo animal experiments, male mice of the CD1 strain, weighing approximately 18–20 grams, purchased from Charles River Laboratories (Wilmington, Mass.) were used. The use of animals in these experiments were in compliance with the Animal Welfare Act and other Federal statues and regulations relating to animals as stated in the National Institute of Health publication: *Guide for the Care and Use of Laboratory Animals*. Mice were infected individually with schistosome cercariae via either tail skin or via shaved abdominal skin. For infection via tail skin, the mouse was restrained in a cage and the tail was dipped for 60 minutes in a tube containing 250–300 $^{35}$S-labeled cercariae suspended in 10 ml of distilled water at room temperature. For infection via abdominal skin, the mouse was restrained on its back. After shaving the abdominal skin, 150–200 $^{35}$S-labeled cercariae were applied to the skin in a drop of distilled water, covered with a cover slip and exposed for 30 minutes.

EXAMPLE 3

Whole Organ Autoradiography

To determine skin penetration and worm establishment, whole tail skin or the area of abdominal skin that was exposed to the cercariae as described above and the lungs were removed from each mouse on day seven after infection and processed for compressed organ autoradiography techniques as described previously (Li J W et al., *Parasitology International* 46: 55–65 (1997)). Briefly, the skin and lungs were mounted on a cardboard sheet, covered with plastic wrap and kept under a tissue press for 48 hrs at room temperature. The pressed and dried tissue was then exposed to X-ray film (Fuji RX, Fisher Scientific, Pittsburgh, Pa.) at −70° C. for 7–9 days. Following autoradiographic development, the dark spots (which represent reduced silver foci on film) were counted and percent worm establishment was calculated (number of spots/total number of cercariae used for infection X 100). Results of these studies show that over about 28% of the effective dose of cercariae penetrated intact skin. Of the total number of cercariae that had entered the skin, over 50% had migrated to the lungs by day 7.

EXAMPLE 4

DEET As A Potent Anti-Penetration Agent Against Schistosome Cercariae

During the past three decades several chemical compounds were screened for their ability to confer protection against cercarial penetration, especially after a skin application. Among these a few compounds such as N,N-diethyl lauramide, Niclosamide, Cederol, hexachlorophere, dibutyl phthalate, and benzyl benzoate were found to have significant cercaricidal effect in vitro. (Naples, J. M., et al., supra, Grenan, M. M., et al., supra; Ghandour, A. M., et al., supra; Fripp, P. J., et al. supra; Abu-Elyazeed R R, et al. Supra) However, except for Niclosamide, none of the other chemicals were tested for their clinical application under field condition.

During studies to screen an appropriate vehicle for skin application of Cederol, a chemical isolated from the cedarwood oil and is shown to have some cercaricidal activity in vitro (Naples J M et al. Supra) against cercariae, it was discovered that N,N-diethyl-m-toluamide(DEET) containing vehicles by themselves were highly effective in preventing cercarial skin penetration. Extensive analysis of each components in the vehicle suggested that the anti-penetrating activity of the preparation was due to DEET.

EXAMPLE 5

In vitro Effects of DEET On *S. mansoni* Cercariae

Based on the foregoing observations, DEET was tested for its effects on *S. mansoni* cercariae. DEET is commercially available and was purchased from Fluka Chemicals Corp. (Ronkonkoma, N.Y.). For in vitro studies, serial doubling dilutions of DEET ranging from 30% to 0.24% were prepared in isopropanol(Sigma, St. Louis, Mo.) and 50 $\mu$l of each dilution was transferred to individual wells of a 96 well flat bottom micro titre plate (Costar, Cambridge, Mass.). Control wells received 50 $\mu$l of isopropanol each. The plates were then kept covered in a fume hood and the fluid was allowed to evaporate overnight. The following day approximately 50 cercariae of *S. mansoni* suspended in 50 $\mu$l of RPMI-1640 media (pH 7.4; Gibco BRL) or phosphate buffered saline (PBS, pH 7.0) was placed in each well and the viability of the cercariae were monitored at 30 min, 60 min, and 4 hrs. A total of 17 replicas were performed for each dilution and for each time point in any one given experiment. To determine the viability of cercariae, 10 $\mu$l of a 0.05% Neutral Red (Sigma Chemical Co.) was added to each well at the end of the experiment and the percentage of live and dead cercariae was determined as described in He et al., *Acta Zoologica Sinica*, 31:240–245 (1985).

Figure 1:
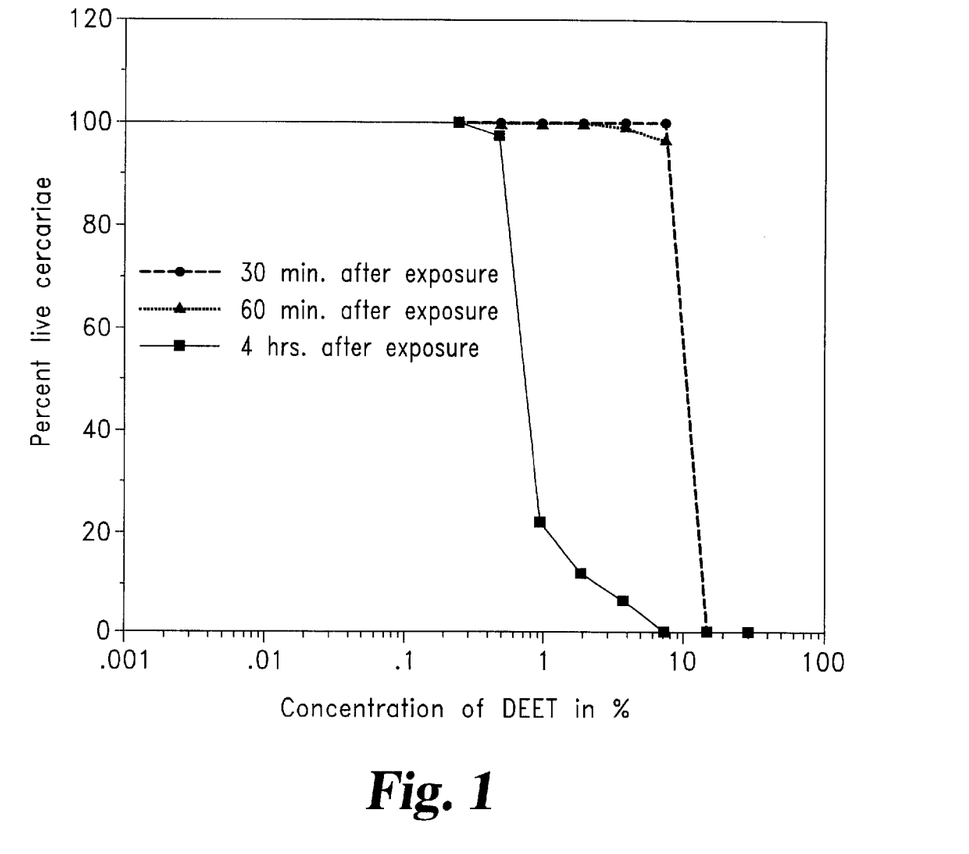
FIG. 1 illustrates the in vitro effects of DEET on *S. mansoni* cercariae. In vitro effects of DEET on cercariae of *Schistosoma mansoni*. Cercariae were placed in 96 well titre plates coated previously with a serial doubling dilutions of DEET ranging from 30% to 0.24%. At different time periods after exposure to DEET, the percent viability of cercariae was evaluated by neutral red exclusion method. The experiment was repeated 17 times with an "n" of 189 to 440 cercariae for each treatment.

These in vitro studies showed that DEET at concentrations of 15% and above was highly lethal for cercariae of *S. mansoni* (FIG. 1). When exposed to such concentrations of DEET cercariae were immediately immobilized. Neutral red staining 30 minutes later confirmed that 100% of cercariae were dead. A time lapse study showed that DEET at concentrations of 7.5% initially immobilized all the cercariae within 5 minutes and by 4 hours 100% of the cercariae were dead. However, concentrations below 7.5% of DEET were less effective in immobilizing or killing cercariae of *S. mansoni*.

EXAMPLE 6

Effect of DEET on the Morphology of Cercariae

Effect of DEET on cercarial morphology was evaluated by transmission electron microscopic studies. In these experiments, approximately 300–500 cercariae of *S. mansoni* suspended in 100 $\mu$l of PBS were placed in each well of a 96 well plate coated with varying concentrations of DEET (ranging from 7.5%–40%) or isopropanol (control) as described above. Samples were collected at 5, 10, 20, 30 and 240 minutes after exposure to DEET and processed for transmission electron microscopy as described in Salafsky et al., *Exper. Parasitol.*, 67:116–127 (1988). Briefly, cercariae collected from each tube were transferred to fresh tubes containing PBS plus 10% fetal bovine serum (Sigma Chemical Co.) and concentrated into a pellet by centrifugation at 500 rpm (300 g) for 5 minutes. The pellet was then fixed overnight at 4° C. in a fixative containing 3% gluteraldehyde, and 1% formaldehyde in a 0.1 M phosphate buffer (pH 7.2). After one hour post fixation in 1% osmium tetroxide the pellet were dehydrated through a graded acetone series and embedded in epon resin. Sections were examined in a Hitachi H-500 transmission electron microscope after staining with uranyl acetate and lead citrate.

Transmission electron microscopic pictures of normal cercariae demonstrated intact, corrugated tegument with an external glycocalyx, single membrane, and an absence of cyton granules. The muscular layer and deeper parenchyma were intact, without edema or degenerative changes.

However, upon exposure to 7.5% DEET, ultrastructural changes of two types were observed: transformative changes that mimic normal changes in the tegument of cercaria during its transformation to schistosomulum, and degenerative changes indicative of severe cellular damage. Both changes were evident as early as five minutes post-exposure, but became more severe with increased duration of exposure. Typical changes after five minutes of DEET exposure include cyton granule migration into the tegument (indicative of transformational changes), diminished quantity of glycocalyx, and early degenerative changes such as intra and extra cellular swelling, diffuse edematous changes in the parenchyma, and focal lysis. These changes were noted in all the parasites examined, although to a varying degree.

Changes progressed in degree at 10 and 30 minutes duration of exposure. Transformative changes with loss of glycocalyx and cyton granule migration, became more prominent, but were generally overshadowed by degenerative changes. Massive accumulation of extracellular fluid was common, causing a flattening of tegument, and focal breaches of the integrity of the tegument was observed. Intracellular degenerative changes of vacuolization, condensation, and disruption of myofilaments in the muscle layer, nuclear swelling and condensation of chromatin, and cellular lysis were progressive over time. Frank lysis of cercariae was observed 240 min after exposure to DEET.

EXAMPLE 7

In vivo Effects of DEET on Cercarial Penetration Through the Skin and Establishment of Infection in Mice In view of the foregoing results, experiments were conducted to determine the effects of DEET on cercarial penetration in vivo.

For application of DEET to the tail skin, mice were individually kept in restraining cages and their tail was dipped in 7.5% DEET solution (prepared in isopropanol) for 5 min. Following application the skin was air dried for 30 min, and rinsed in distilled water for 1 min before exposure to radio-labeled cercariae of S. mansoni as mentioned in Example 3.

For application of DEET to the abdominal skin, mice were restrained to the back and their abdomen shaved. 200 $\mu$l of an appropriate concentration of DEET in isopropanol solution was dropped on to the abdomen and allowed to dry for 15 min. After drying, the skin was washed for 1 min with distilled water and exposed to radio-labeled cercariae for 30 min.

Results of the in vivo studies showed that in controls animals that were treated with only isopropanol, a significant proportion (over 28%) of the infective dose penetrated intact skin. Of the total that has entered the skin over 50% had migrated to the lungs by day 7. Application of 7.5% DEET to the skin before infection resulted in a significant reduction in the ability of the parasite to penetrate intact skin. These results show that only 0.13% of the total infective dose managed to penetrate the 7.5% DEET coated skin (Table 1). However, their ability to migrate to the lungs was completely lost after treatment with 7.5% DEET (Table 1). This suggested that 7.5% DEET is a potent anti-penetration agent against cercariae of schistosomes.

TABLE 1

Effect of DEET on Cercarial Entry into the Skin of Mouse and Establishment of Infection.

| Groups | Percent Worm Established | | |
|---|---|---|---|
| | Skin | Lungs | Total |
| Control | 9.9 ± 1.2% | 18.6 ± 4.1% | 28.5 ± 6.4% |
| 7.5% DEET | 0.13 ± 0.01% | 0 | 0.13 ± 0.01% | n = 10

EXAMPLE 8

Effect of Various Concentrations of DEET On Cercarial Penetration and Worm Establishment The experiment described in Example 7 was repeated with varying concentrations of DEET (5%, 10%, 20%, 40%). At 5% the protection was only 72% suggesting that this concentration of DEET is not completely effective, whereas DEET when applied to the skin at concentrations of 10, 20 or 40% was 100% effective in preventing the entry of cercaria into the mouse skin. These studies thus confirmed the above results and showed that DEET could be successfully used to prevent infections with S. mansoni.

EXAMPLE 9

Effect of DEET After Exposure to Infections with S. mansoni

In order to determine whether DEET had any effect on cercarial penetration and migration after exposure to cercariae, we applied 40% DEET to the skin at various time periods after infection. It is well established that after entry, the parasite remains in the skin for 24–72 hrs before migrating to the lungs. Therefore, experiments were conducted to determine if DEET is still capable of killing the parasites if applied to the skin after exposure to the infection. If effective, potential accidental exposure to the infection could be treated with DEET. Mice were infected with radiolabelled cercariae via abdominal skin (as described in example 2) and 40% DEET was applied to the site of infection 30 min, 4 hrs, 24 hrs or 48 hrs later. Worm establishment was determined by compressed organ autoradiography (as described in Example 7). These studies showed that DEET when applied to the skin within 30 min after exposure to the cercariae was 100% effective in preventing the infection. However, application of DEET to the skin 4 hrs or more after infection conferred no protection. These results showed that DEET could be used effectively in controlling schistosomiasis even up to 30 minutes post exposure to the infection.

EXAMPLE 10

Duration of Activity of DEET After a Single Skin Application

Experiments were also conducted to see how long the cercaricidal activity of DEET remained in the skin after a single application. In these experiments 10% DEET was applied to the shaved abdominal skin of mice and was allowed to dry. Thirty minutes after DEET application, the area of skin was washed continuously for one minute with running distilled water. At different time points (30 min, 1 hr, 4 hrs, and 24 hrs) after DEET application, mice were infected with radio-labeled cercariae (as described in Example 2) and worm establishment was determined by compressed organ autoradiography (as described in Example 3). These studies showed that exposure to infection 30 min, one hour and four hours after DEET application conferred 100%, 98±1% and 85±1% protection respectively against schistosomiasis. However, exposure to infection 24 hrs later conferred no protection at all. These results thus suggested that the effect of DEET in the skin lasts only for a short duration of time, that is from 30 min to one hour.

EXAMPLE 11

Formulations for Prolonging Effects of DEET in the Skin

In an attempt to identify a suitable vehicle that will retain the activity of DEET for a longer duration of time in the upper layers of skin, especially in the stratum corneum, we analyzed the ability of Polyolprepolymer 2 (Penederm Incorporated, Foster City, Calif.; distributed by Barnet Products Corp. Englewood Cliffs, N.J.), Polyolpolymer 15 (Barnet Products Corp.) and positively charged liposome kit (L-α-phosphatidyl choline 63 $\mu$mols, stearylamine 18 $\mu$mols, cholesterol 9 $\mu$mol, lot 47H8350, Sigma catalogue number L-4395). Pp2deet (preparations containing 10% DEET plus 10% polyolprepolymer 2 in isopropanol) was made by adding 1 ml of 100% DEET solution to 9 ml of 10% polyolprepolymer2 in isopropanol and vortexing vigorously for 10 minutes at room temperature. Pp15deet (10% DEET plus 10% polyolprepolymer 15 in isopropanol) was prepared in a manner similar to Pp2deet.

Other concentrations of polyolprepolymers and DEET are also useful in the practice of the invention. For example polyolprepolymer concentrations may range from about 1% w/v to about 70% w/v although about 10% w/v is preferred.

Positively charged multilamellar lipodeet was prepared by adding 1.0 ml 100% DEET to 63 $\mu$mols of L-α-phosphatidylcholine, 18 $\mu$mols of stearylamine and 9 $\mu$mols of cholesterol. The mixture was well mixed until a uniform solution was formed. A 10% solution of the multilamellar lipodeet micelle was then prepared by adding 9.0 ml of phosphate buffered saline (PBS) to the mixture and vortexing vigorously for 10 minutes at room temperature. The lipodeet mixture was then allowed to stand for 10 minutes at room temperature. The size and structure of the micelle were observed under a microscope (×100) to confirm uniformity. Liposomes according to the present invention do not require the presence of an anchor molecule such as sodium pyridinethione as is required by the liposomes of U.S. Pat. No. 5,173,303, and which incorporated herein by reference.

Figure 2:
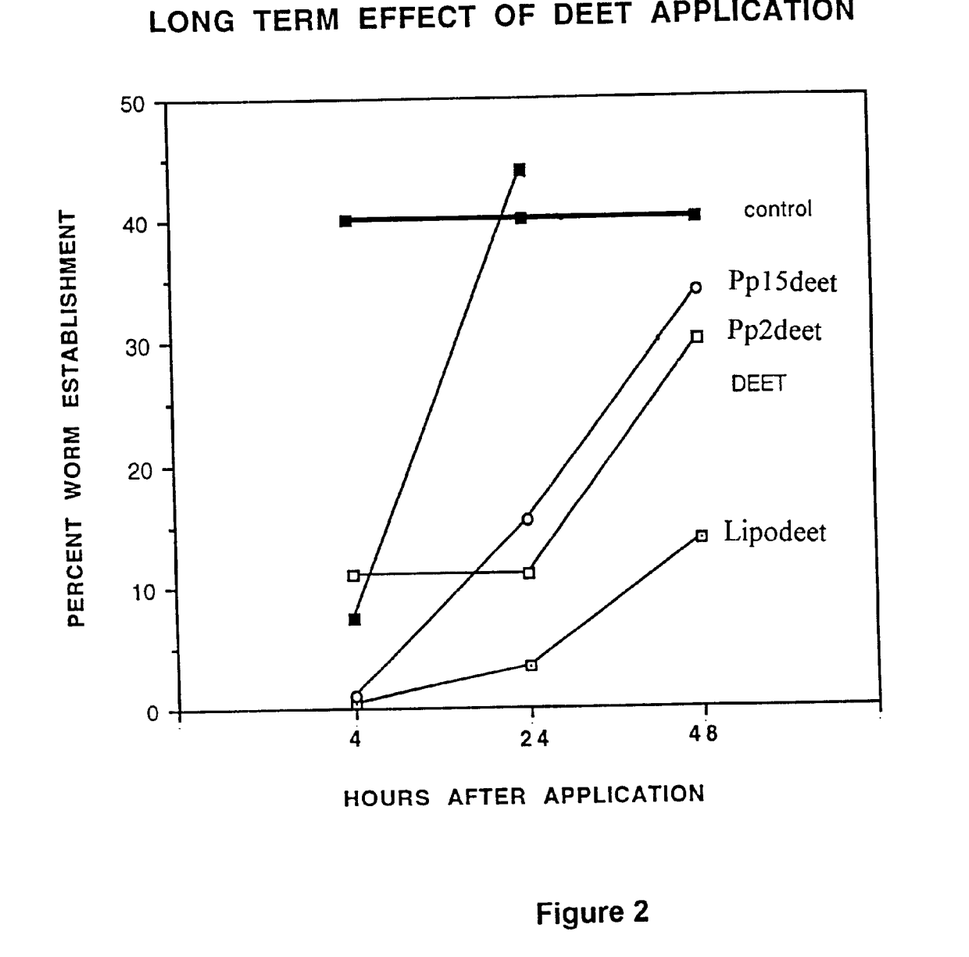
FIG. 2 illustrates the in vivo effects of lipodeet on *S. mansoni* cercariae. 100 µl if 10% solution of a positive lipodeet preparation was applied to the shaved abdominal skin of mice and allowed to dry for 15 min. At various time periods (4 hrs, 24 hrs and 48 hrs) after the lipodeet had dried in the skin, the skin was washed for one minute in a continuous flow of distilled water and infected with 300 $^{35}$S-labeled cercariae of *S. mansoni*. Seven days after infection, number of parasites in the skin and the lungs were determined by compressed organ autoradiography.

To determine the effect of the formulations on cercarial penetration and migration, vehicles, Pp2deet, Pp15deet or Lipodeet was applied to the abdominal skin as detailed in example 7. At different time points after skin application (4 hours, 24 hrs or 48 hrs) mice were infected with radio-labeled cercariae and worm establishment was measured by compressed organ autoradiography. These studies showed that compared to DEET alone, all the three vehicles tested prolonged the effect of DEET in the skin for up to 48 hours. The results are represented as FIG. 2. Of the three vehicles tested, the lipodeet appeared to be more efficient in retaining the activity of DEET to the skin than the polyolprepolymers, although all three compounds were used effectively. These data establish that formulation of the present invention, long acting preparations of DEET, allow the retention of the activity of DEET in the skin for a longer duration of time, thus minimizing its absorption and catabolism and toxicity.

Other preparations of liposomes that differ in charges (positive, negative and neutral references to those liposomes), or that differ in the composition of the hydrophilic molecule (a water soluble broad spectrum anthelmintics such as praziquantel or thiabendazole instead of PBS), can be used to provide a combination therapy/prophylactic formulation, with or without DEET.

EXAMPLE 12

Quantitation and Localization Amount of DEET Formulations in the Skin

Quantitation and evaluation of the amount of DEET retained in the skin when administered in the lipodeet formulation and identification as to which layers of the skin DEET is localized is accomplished using a $^{14}$C-labeled lipodeet preparation ($^{14}$C-DEET plus positively charged liposomes and described above). Disposition of DEET in various layers of the skin (as determined by histological staining) are measured by scintillation counting and by autoradiography. The formulation is applied to the skin and pieces of skin are removed at various time periods (30 min, 4 hrs, 8 hrs, 24 hrs, 48 hrs and 72 hrs) after application and are evaluated. These studies showed that at 30 min, 4 hrs and 8 hrs after application 100% of the $^{14}$C-Lipodeet were present in the superficial layers of the skin. Scintillation counting after 24 hrs showed that 84±2% of $^{14}$C-Lipodeet was still present in the skin. Analysis at 48 and 72 hrs showed that there is a gradual decrease in the amount of $^{14}$C-Lipodeet in the skin (52±12% and 36±17% respectively). These results were confirmed by skin strip techniques as described in Artmann et al., *Drug Research*, 40:12–28 (1965). These studies showed that over 91% of $^{14}$C-Lipodeet is retained in the stratum corneum during the first 24 hours after single application.

EXAMPLE 13

Effect of DEET on Ticks

To determine the effect of DEET on tick attachment and feeding we used two species of ticks *Amblyoma americanum* and *Dermacetor variabilis* purchased from University of Oklahoma. Ticks were allowed to feed on the ears of male New Zealand white rabbits purchased from Charles River. For feeding, five ticks were introduced into a 60 $\mu$m sieve cell well (Fisher Scientific) which was attached to the ear of the rabbit with nail glue. Ticks were observed every 30 minutes for the first eight hours to assess skin attachment and feeding behavior. Tick attachment was defined as the minimum time required for 3 of the 5 ticks to attach to the ear. If the ticks did not attach, even after 24 hours, they were removed and five new ticks were introduced in the same well and observed as previously. The observation was continued for 72 hours for both species of ticks. Separate rabbits were used for each species and for each treatment. Results show that the attachment time for Dermacetor and Amblyoma to the ear of normal rabbits was 4.5 hours and 20 hours respectively. However, applications of 10% DEET to the ear prior to the introduction of ticks resulted in no tick attachment for the initial 7.0 hours in the case of dermacetor and for initial 22.0 hours for Amblyoma. This suggests that DEET is effective for a few hours over respective baselines. All the ticks in this study were active until attachment. These results confirm earlier studies that DEET is an effective repellant against tick biting, although the effect is short-lived.

EXAMPLE 14

Effect of Lipodeet on Ticks

To determine the effect of long-acting lipodeet on tick attachment and feeding behavior, 100 μl of a preparation of 10% lipodeet as describe above was applied to the dorsal skin of rabbit ear and five ticks were introduced into each sieve cup as described in Example 13. Ticks were monitored every 30 minutes for the first eight hours and thereafter every 24 hours. Five fresh ticks were introduced every 24 hours for up to 72 hours. In these experiments the same two species of ticks were used as described in Example 13. Results show that the ticks failed to attach to the skin even up to 72 hours after lipodeet application. All the ticks introduced during the first 48 hours were dead within five hours after introduction, suggesting that 10% lipodeet was lethal to the ticks. Of the ticks introduced after 48 hours, 3 of the 5 were dead within five hours, and the remainder unattached up to 72 hours. These results show that lipodeet is 100% effective against tick bites for up to 72 hours after a single application.

EXAMPLE 15

Effect of Lipodeet on Other Biting Insects

Formulations of the present invention are also useful as repellants against other biting anthropod vectors such as sand flies, mosquitoes and bugs that transmit deadly infections in both human and animals. Experimental hosts such as mice (for bugs) dogs (for sand flies) and human (mosquitoes) are well known in the art. Such host animals are treated with the formulations of the present invention and the ability of the arthropod vectors to feed on the host are evaluated. Appropriate dosages of the formulations are readily determined by methods such as those described above well known in the art.

EXAMPLE 16

Wash-off Tests with DEET and Lipodeet in Schistosomaisis

The present series of experiments was carried out to evaluate the effect of washing with water and/or remaining in water on the protective effect of DEET and Lipodeet given the fact that water contact is a must in acquiring schistosomiasis. Furthermore, given that schistosomiasis is prevalent in tropical or subtropical climates, the effect(s) of water temperature on the retention of the protective effect of DEET and Lipodeet was also tested.

Experiments were set up wherein two concentrations of Lipodeet (10% and 20%) were applied (100 μl/mice) to the abdominal skin area (approximately one square inch) of two groups (n=40) of mice and allowed to dry for 30 min. Following the application, 10 mice each were allowed to swim and bathe in water (maintained at 29° C. or 37° C.) for a period of 5 min or 60 min in a small trough kept in an incubator. After bathing, mice were allowed to dry completely. The abdominal skin of these mice was then exposed to 150 cercariae of S. mansoni labeled with $^{35}$S-methionine. Degree of protection conferred by Lipodeet and DEET after the wash off treatment was evaluated by monitoring the entry of parasites into the skin by compressed organ autoradiography techniques as described earlier (Li et. al. *Parasitology International* 46:55–65, 1997).

Results of these experiments show that 10% DEET is easily washed off the skin. Surprisingly, even five minutes of exposure to water significantly ($p<0.01$) abolished the protective effects of DEET, irrespective of the water temperature. In contrast, a similar study with 10% Lipodeet showed that a significant amount of the protective effect of Lipodeet remained in the skin even after a wash off for 60 minutes with water at 37° C. Increasing the concentration of DEET to 20% slightly improved the retention of protective ability of DEET even after the wash off. Interestingly, increasing the concentration of Lipodeet to 20% gave greater than 90% protection even after one hour wash off at 37° C. These studies thus confirm that Lipodeet is not easily washed from the skin, and hence, will be a superior pharmacological agent for preventing infections with schistosomiasis in human and animals.

EXAMPLE 17

Comparison of the Efficacy of Different Concentrations of DEET and Lipodeet Against Ticks In this series of experiments, the protective effect(s) of different concentrations of DEET and Lipodeet on the attachment of nymphs and adults of two species of ticks, *A. americanum* and *D. variabilis*, to the rabbit ear was evaluated. Experiments were set up wherein different concentrations (20% or 40% of DEET or Lipodeet were applied (0.2 ml of the samples to 10 $cm^2$ surface area), onto the dorsal side of the ear lobes of a rabbit. After allowing the preparation to dry for 30 min., sieve cups (Fisher Scientific, 1" inner diameter) were then attached to the ear lobes using nail glue. Ten nymphs or five adult ticks were then introduced into the sieve cups every 24 hrs through a small slit made on the sieve membrane. Attachment of ticks to the skin was monitored every 24 hrs. for up to 72 hrs. after introduction of the ticks.

Results of these studies show that without any treatment, 40% of *A. americanum* nymphs attached to the rabbit ear. However, topical application of 20% DEET to the skin significantly (50%) reduced the attachment of *A americanum* nymphs to the rabbit ear from 24 to 72 hrs. In contrast, application of 20% Lipodeet completely prevented (100%) nymph attachment to the rabbit ear for up to 48 hrs. By 72 hrs., however, 5% of nymphs managed to attach themselves demonstrating that Lipodeet formulation is more efficient in preventing attachment of *A. americanum* nymphs to the rabbit skin than DEET by itself. Increasing the concentration of DEET and Lipodeet to 40% increased their protective ability. 40% DEET completely prevented tick attachment to the skin by up to 24 hrs. However, by 48 hrs, 20% of the ticks were found attached to the skin suggesting that the effect of DEET is short lived. Application of 40% Lipodeet to the skin completely (100%) prevented attachment of *A. americanum* nymphs to the rabbit skin for up to 72 hrs. This suggested that Lipodeet is an excellent long-acting formulation of DEET that can prevent attachment of *A. americanum* nymphs to its host for up to three days after a single application. Physical examination of the nymphs after the experiment revealed that more than 50% (18 out of 30) of the nymphs were dead. These findings also suggest that Lipodeet may be a contact lethal agent for *A. americanum* nymphs.

Effects of Lipodeet on adult Amblyoma ticks were much more dramatic than the nymphs. Without any treatment, 100% (5.5) of ticks attached to rabbit ears within 24 hrs. Five new ticks that were introduced every 24 hrs. also attached to the skin within 24 hrs. of their introduction. Thus, at the end of the experiment, 15 out of 15 (100%) adult A. americanum ticks attached to the untreated rabbit ear. Topical application of 20% DEET prevented tick attachment for up to 24 hrs. However, by 48 hrs., 20% of the ticks (2/10) attached to the skin and by 72 hrs., 40% of the ticks (6/15) had attached to the rabbit ear. These data again suggested that the effect of DEET is A. americanum adult ticks attached to the rabbit ear. Only 10% (1/10) of ticks were found attached to the ear at 48 hrs. and by 72 hrs., 20% (3/15) of the ticks were attached. Topical application of 20% or 40% Lipodeet completely (100%) prevented attachment of adult short lived. Increasing the concentration of DEET to 40% significantly reduced the number of adult A. americanum ticks to rabbit ears for up to 72 hrs. These results suggest that Lipodeet is an excellent long-acting formulation that prevents tick attachment to the skin.

Similar experiments were carried out using nymphs and adults of D. variabilis ticks. These results show that 20% DEET was effective in preventing attachment of D. variabilis nymphs to the rabbit ear for up to 48 hrs. but was effective only up to 24 hrs. against adult ticks. Increasing the concentration of DEET to 40% had no added advantage against nymphs. However, against adult ticks, 40% DEET was slightly more effective at 48 hrs. that 20% DEET. A single topical application of Lipodeet was highly effective against both nymph and adults of D. variabilis. Both nymphs and adults of D. variabilis failed to attach to the rabbit skin for up to 72 hrs. after application of a single does of 20% or 40% Lipodeet. These results confirm that Lipodeet is an excellent long-acting formulation of DEET that repels tick attachment for up to three days after a single skin application.

More than 60% of ticks used in our experiments were dead after contact with Lipodeet. Although a well-aerated sieve cup was used (1" inner diameter), we initially thought that the tick mortality may be due to possible DEET vapor trapped within the sieve cup. Therefore, we designed experiments where one half of the surface area of skin within the sieve cup was treated with 40% Lipodeet and the other half was left untreated. Five adults ticks of A. americanum were then introduced into the sieve cups every 24 hrs. After 72 hrs., the sieve cups were removed. Interestingly, all the ticks that were introduced into the sieve cups were found attached to the untreated skin. Similar results were obtained with D. variabilis as well. However, when the experiments were repeated with 40% DEET, ticks were seen attached to both treated and untreated surfaces within the sieve cups.

EXAMPLE 18

Absorption of DEET and Lipodeet Through Skin

One of the major problems associated with use of DEET is its potential toxicity if absorbed in large quantities. Currently available preparations of DEET are contained in vehicles that inevitably increase the absorption of DEET through the skin. This potentially increases the risk of DEET-induced toxicity. We designed two different sets of experiments to evaluate what percentage of DEET and Lipodeet, a DEET formulation in liposomes, remained in the skin and what percentage is absorbed systemically through the skin. These studies also compared the relative toxicity of DEET and Lipodeet.

In the first series of experiments, 200 µl of 60% DEET or 60% Lipodeet was applied to the abdominal skin (3 cm$^2$ surface area) of mice (n=60). At different time intervals (15 min, 30 min and 60 min) after application, groups of mice (n=20) were sacrificed and plasma samples were collected to quantify the level of DEET by high performance liquid chromatography (HPLC) analysis. Prior to HPLC analysis, DEET present in the plasma samples was extracted using a C1 8 column (Bond-Elute, Varian Analytical Supplies Co., Harbor City, Calif., 100 mg, 1 ml). Briefly, the Bond-Elute cartridges were activated by washing with two ml of HPLC grade acetonitrile (Sigma chemicals Co., St. Louis, Mo.) followed by two ml of deionized, degassed filtered water. A low vacuum (<0.5 in Hg) was applied for the wash using a Vac-Elute manifold (Varian Analytical Supplies Co.). Following activation, on ml of plasma samples was passed through the C18 cartridges using a low vacuum (<0.5 in. Hg). The cartridge was then washed with three mls. of acetonitrile-ammoniumacetate (pH 4.5, 0.03 M, at 40:60 V:V) under low vacuum (<0.5 in. Hg). The eluant was then injected directly onto columns (ODS-1, 250×4.6 mm, Alltech Co., Deerfield, Ill.) for HPLC analysis (Waters, Division of Millipore, Milford, Mass.). Chromatographic conditions used for HPLC analysis is as follows: Mobil phase: acetonitrile-ammoniumacetate (pH 4.5, 0.03M, at 36:64 v:v), flow rate 1.0 ml/min, UV detection at 220 nm. Sensitivity was set at 0.01AUFS. Ammonium acetate was used as the internal standard.

Results of these studies show that 11.6 mg (9.7%) of DEET was present in the plasma within 15 minutes after application. By 30 minutes, 5.3 mg (4.4%) could be recovered in the plasma, and in one hour, nearly 0.182 mg (0.15%) DEET was present in the plasma. Previous studies (Selim et al. *Fundamentals of applied Toxicology* 25:95–100, 1995) show that DEET is metabolized within minutes of absorption and is excreted mainly via urine. Although we did not measure the amount of DEET that is excreted via urine, it is clear from our results that a substantial quantity of DEET is absorbed through the skin within few minutes after a single skin application. A similar application of Lipodeet resulted in significantly lower absorption of DEET through the skin. Amount of DEET absorbed through the skin from a formulation of Lipodeet was 0.21 mg (0.17%) at 15 min, 0.28 mg (0.23%) at 30 min, and 0.06 mg (0.05%) at 60 min. These data suggest that DEET when applied as a Lipodeet formulation is poorly absorbed through the skin. It is well established that liposomes once applied to the external surface, can penetrate into all skin layers and hold the active ingredients to the site for a prolonged period of time. This may explain why Lipodeet is poorly absorbed through the skin thus providing a longer duration of DEET action at the skin surface.

These results were further confirmed using radio-labeled DEET ($^{14}$C-DEET, specific activity 1.88 Ci/mmol, 0.996 g/ml) purchased from Sigma. In this series of experiments, 11.472 mg of $^{14}$C-DEET of $^{14}$C-Lipodeet (in 100 µl) was applied to 5 cm$^2$ area of the mice abdominal skin. At different time points (15 min, 30 min, 60 min, 2 hrs., 4 hrs., 24 hrs., 48 hrs. and 72 hrs.) after application, the whole area of skin where the lipodeet had been applied was collected, underlying tissue removed and the radioactivity measured in a Beckman β-counter. Samples of blood and urine were also collected at these time points from each mouse to measure the radioactivity (n=10 for each time point). Results of these studies show that with time there was a steady decrease in the amount of DEET present in the superficial layers of the skin. By 24 hrs. nearly all of the DEET applied to the skin has been cleared from the superficial layers. However, a similar application of Lipodeet resulted in the retention of nearly 100% of DEET in the superficial layers of the skin for up to 4 hrs. after a single application. During the span of 4 hrs. to 24 hrs., there was a sharp decline in the amount of Lipodeet retained in the skin. By 24 hrs., only about 10% Lipodeet was present in the skin. However, interestingly this small quantity of Lipodeet was retained in the skin for a longer period of time. In this study, we made observations only up to 72 hrs. This suggested that after a single application a small quantity of Lipodeet remains as a depot in the skin. This residual Lipodeet is potentially prolonging the functional activity of DEET in the skin. It was a bit surprising that 100% of DEET and nearly 90% of the Lipodeet are lost from the skin during 4 to 24 hrs. after application. There are two possibilities, (1) substantial quantities of both DEET and Lipodeet are absorbed systemically through the skin within 24 hrs., or (2) both the chemicals are lost in the bedding due to direct contact of the applied area to the bedding materials. The first hypothesis was tested by measuring $^{14}C$ levels in the blood and urine in these animals. Significant quantity of the radio label was present in the blood of animals within 15 minutes after applying $^{14}C$-DEET. Although we did not have an earlier time point, urine collected from these animals at 15 minutes was highly radioactive (>5.7×$10^7$ cpm/ml) suggesting that significant quantity of DEET is absorbed from the skin as is metabolized within 15 minutes of application. However, a similar analysis on animals treated with Lipodeet showed that a very small quantity of Lipodeet is absorbed through the skin. Urine from these animals was radioactive only at two hrs. after application, and then, at levels that were much lower (<1.2×$10^3$ cpm) than the DEET treated group suggesting that very little Lipodeet is absorbed through the skin until 2 hrs. after application. From 4 hrs. to 72 hrs. practically no radioactivity could be measured in the blood or urine of Lipodeet treated animals. Yet there was a sharp decline in the amount of radioactivity in the skin after 24 hrs. Surprisingly, when we measured the radioactivity in the bedding, we found that the bedding of both the group of animals was highly radioactive. However, bedding from the Lipodeet group was 50 times more radioactive than the DEET group. These results suggested that most of the Lipodeet is lost externally from the skin either by contact or by shedding. This huge loss may be partially due to the fact that the mouse skin, and stratum corneum in particular, is comparatively thin and this limits the amount of Lipodeet it can hold. This may explain why approximately 10% of Lipodeet is retained in the skin for a very long time. These data together with the HPLC data clearly show that very little Lipodeet is absorbed through the skin. The residual Lipodeet remaining in the skin as a depot confers the long-acting action against *S. mansonii* and ticks.

EXAMPLE 19

Laboratory Evaluation of Lipodeet as a Mosquito Repellant for Human Use

The above studies demonstrate that DEET and Lipodeet is effective against the skin penetrating parasites, schistosome and two species of ticks. However, one of the major uses of DEET is against mosquitoes. Therefore, we wanted to test whether Lipodeet prolongs the mosquito repellency activity of DEET. These experiments were conducted on human volunteers at the Illinois Natural History Survey Center for Economic Entomology, University of Illinois Urbana-Champaign. Five different concentrations of Lipodeet (10%, 15%, 30% and 40%) or three different concentrations of DEET (10%, 30% and 40%) were evaluated for their repellency action against *Aedes aegypti* species of mosquitoes. The test solutions were applied to 8.5 cm area (1.76 μl/cm²) on the forearm of the subjects and the duration of repellency against the mosquitoes was evaluated over a period of 24 hrs. No treatment was applied to the other forearm and this remained as controls. Paper cups (1 pint) screened at one end with a fine mesh and closed at the other end was used as test cages in this study. Fifteen to twenty female *A. aegypti* at three to seven days after their emergence were introduced into each test cage and the screened end of the test cage was held against the forearm for one to three minutes at different time intervals (0, 0.5 hrs., 1 hr, 2 hrs., 6 hrs. and 24 hrs.). Five minutes after application of the samples were treated as time 0. After the exposure, mosquitoes were removed and the number that were blooded were counted. Values were expressed as follows:

$$\text{Percent repellency} = \frac{(\text{Number of controls blooded} - \text{number of treatments blooded})}{\text{Number of controls blooded}} \times 100$$

Human study was conducted with the prior approval of the IRB at the University of Illinois at Urbana-Champaign.

Results of these studies showed that Lipodeet is more efficient than DEET in repelling *A. aegypti* mosquitoes. In these studies, the effect of 10% or 30% DEET was completely lost by six hours, whereas, the effect of 10%, 15% or 30% Lipodeet lasted longer than 6 hours. More than 50% repellency was seen even at 12 hrs. after a single application lasted for nearly 24 hrs. Although normally under field condition the effect of DEET last only for eight hours, in the above preliminary study repellent activity of Lipodeet was evident even up to 24 hrs. after a single application under laboratory conditions. Further field trials need to be conducted to confirm these results.

EXAMPLE 20

Formulations of DEET and Lipodeet with Other Insect Repellants

Also envisioned within the scope of the present invention are formulations of DEET, DEET analogs or Lipodeet with one or more insect repellants in suitable delivery vehicle(s) to increase the degree and time of repellency to a variety of biting insects. A preferred embodiment of the present invention includes DEET and DEET analogs in formulations with one or more insect repellant congeners selected from a group of congeners that include 1-(3-cyclohexene-1-ylcarbonyl)-2-methylpiperidine (AI3-37220), N-(1-methyl propoxycarbonyl)-2-(2-hydroxyethyl)piperidine, p-menthane-3,8-diol, ethyl-3-(N-n-butyl-N-acetyl) aminopropionate, 1-(3-cyclohexene-1-ylcarbinyl) piperidine, N,N-diethyl benzamide, N,N-diethyl mandelamide, (2-hydroxymethylcyclohexyl)acetic acid lactone, 1S, 3S, 4S, 6R-carane-3,5-diol, and 1-piperidinecarboxylic acid 2-(2-hydroxyethyl)-1-methyl propylester to increase the degree and time of repellence to insects of different species. Appropriate dosages of DEET, DEET analogs, and congeners in the formulations are readily determined by methods such as those described above and well known in the art.

The formulations include DEET or DEET analogs, and one or more of the congeners listed above in a suitable delivery vehicle that will retain the activity of the formulation for extended period of time in the upper layers of the skin, especially stratus corneun. Such delivery vehicle(s)

include polyolprepolymer 2 (Penederm lucor Purated, Foster City, Calif.); polyolpolymer 15 (Barnet Products Corp.); and positively charged liposome kit (L-X-phosphatidyl choline 631 μmols, stearglamine 18 μmols, cholesterol 9 μmols) 101-47H8350, (Sigma catalogue number L-439G). Pp2DEET and Pp5DEET preparations containing one or more of the congeners described above will be prepared as previously described (See Example 11). Positively charged multi-lamellar lipodeet-congener preparation are prepared as previously described (See Example 14).

Effect of the formulations Pp2DEET-congener, Pp15DEET-congener or lipodeet-congener on cercarial penetration will be assessed using the procedure detailed in Examples 7 and 11. Formulations of the present invention are also useful as repellants against other biting arthropod vectors such as sand flies, mosquitoes and bugs that transmit deadly infections in both human and animals. Experimental hosts such as mice (for bugs), dogs (for sand flies), and human (for mosquitoes) are well known in the art. Such host animals are treated with the formulations of the present invention and the ability of the arthropod vectors to feed on the host are evaluated.

The foregoing examples are presented by way of illustration and are not intended to in any way limit the scope of the present invention as set out in the appended claims.

LITERATURE CITED

The references cited below are incorporated herein by reference.

Artman, C, Roding J, Ghyczy M, Liposomes from soya phospholipids as percutaneous drug carriers. Qualitative in vivo investigations by macromolecules and salt-loaded liposomes with radioactive labeling. *Drug Research* 40: 12–28, 1965.

Abou-Donia M B, Wilmarth K R, Jensen K F, Oehme F W, Kurt T L, Neurotoxicity resulting from coexposure to pyridostygmine bromide, deet, and permethrin: implications of Gulf war chemical exposures. *Journal of Toxicology and Clinical Toxicology* 32:1–16, 1996.

Abu-Elyazeed R R, Podgore J K, Mansour N S, Kilpatric M E, Field trial of 1% Niclosamide as a tropical antipenetrant to Schistosoma mansonii cercariae. *American Journal of Tropical Medicine and Hygiene* 49: 403–409, 1993.

Bar-Zeev M, Gothilf, S, Laboratory evaluation of flea repellants. *Journal of Medical Entomology* 9: 215–218, 1972.

Couch P, Johnson C E, Prevention of Lyme disease. *American Journal of Hosp. and Pharm.* 49: 1164–1173, 1992.

Dorman D C, Diethyltoluamide (DEBT) insect repellant toxicosis. *Veterinary Clinics of North American Small Animal Practice* 20: 387–391, 1990.

Elias P M, Lipids and the epidermal permeability barrier. *Archives of Dermatological Research*. 270: 95–102, 1981.

Fripp P J, Armstrong F L, The efficacy of a hexachlorophene skin cleanser as a cercarial repellant. *South African Medical Journal* 47:526–527, 1974.

Ghandour A M, Webbe G., The effect of sublethal concentration of the molluscide niclosamide on the infectivity of Schistosoma mansonii cercariae. *Journal of Helminthology* 49:245-25-, 1975.

Grenan M M, Greene L K, Davidson, D E Jr., Jones D H, Hexachlorophene as a topically applied chemical for prophylaxis against Schistosoma mansonii infections in mice. *Rev. Inst. Med. Trop. Sao Paolo* 27: 190–196, 1985

He Y X, Mao C S, Hu Y Q: Comparison of some physiological aspects between cercariae and newly transformed schistosomula of *Schistosoma japonicum*. *Acta Zoologica Sinica* 31:240–245, 1985.

Kumar S, Prakash S, Kaushik M P, Rao K M, Comparative activity of three repellants against the ticks *Rhipicephalus sanguineus* and *Argus persius*. *Medical Veterinary Entomology* 6:47–50, 1992.

Li J W, Ramaswamy K, Salafsky B, He Y X, Shibuya T: Trans$^{35}$S-labeling of cercariae of *Schistosoma mansonii*: a less expensive tool for tracing in vivo migration of schistosomula in mice. *Parasitology International* 46:55–65, 1997.

Mehr Z A, Rutledge L C, Inase, J L, Evaluation of commercial and experimental repellants against Xenopsylla cheopsis (Siphonoaptera: Pulicidae). *Journal of Medical Entomology* 21:665–669, 1984.

Monika-Hildegard S, Korting H C, Liposomes as penetration enhancers and controlled-release units. In "*Percutaneous penetration enhancers.*" eds., E. W. Smith and H. I. Maibach, CRC Press, New York, 1995.

Naples J M, Schiff C J, Rosier K H, *Schistosoma mansonii*: cercaricidal effects of cedarwood oil and various of its components. *Journal of Tropical Medicine and Hygiene* 95: 390–396, 1992.

Salafsky B, Ramaswamy K, He Y X, Anderson G L, Nowicki D K, Shibuya T: Evaluation of N,N-diethyl-m-toluamide (DEET) as a topical agent for preventing skin penetration by cercariae of *Schistosoma mansonii*. *American Journal of Tropical Medicine and Hygiene* 58:828–834,1998.

Salafsky B, Fusco A C, Whitely K, Nowicki D, Ellenberger B: *Schistosoma mansonii*: Analysis of cercarial transformation methods. *Experimental Parasitology* 67:116–127, 1988.

Santus G C, Baker R W, Transdermal enhancer patent literature. *Journal of Control Release Substances*. 25:1–27, 1993.

Solberg V B, Klein, T A, McPherson K R, Bradford B A, Field evaluation of DEET and a piperidine repellant (A13-37220) against Amblyoma americanum (Acri: Ixodidae). *Journal of Medical Entomology* 32: 870–875, 1995.

Veltri J C, Osimitz T G, Bradford D C, Page B C, Retrospective analysis of calls to poison control centers resulting from exposures to the insect repellant N,N-diethyl-m-toluamide (DEET) from 1985–1989. *Journal of Toxicology and Clinical Toxicology*. 32:1–16, 1994.

Verschoyle R D, Brown A W, Nolan C, Ray D E, Lister T, A comparison of the acute toxicity, neuropathology, and electrophysiology of N,N-diethyl-m-toluamide and N,N-dimethyl-2,2-diphenylacetamide in rats. *Fundamentals of Applied Toxicology* 18:79–88, 1992.

Wang, J C., Delivery systems of cosmetic ingredients: technology, trends, and market opportunities. *Drug and Market Development* 8:166, 1997.

WHO Expert Committee on the Control of Schistosomiasis: Public health impact of Schistosomiasis: Disease and mortality. *Bulletin of the World Health Organization* 71:657–662, 1993.

We claim:

1. An insect repellant and antiparasitic composition comprising a liposome and N,N-diethyl-m-toluamide (DEET), said liposome having a phospholipid-containing membrane entrapping an aqueous medium, wherein said DEET is interspersed with phospholipids of said membrane, and wherein said aqueous medium comprises a water-soluble anthelmintic drug.

2. The composition of claim 1, wherein the liposome comprises a naturally occurring glycerophospholipid.

3. The composition of claim 1, wherein the liposome comprises a multilamellar liposome micelle.

4. The composition of claim 2, wherein the liposome comprises a multilamellar liposome micelle.

5. The composition of claim 1, which exhibits activity against skin penetrating parasites and insects for over 48 hours after application to the skin.

6. The composition of claim 5, wherein the liposome comprises a naturally occurring glycerophospholipid.

7. The composition of claim 1, wherein the composition comprises from about 1% w/v to about 50% w/v DEET.

8. The composition of claim 1, wherein the composition comprises from about 7.0% w/v to about 10% w/v DEET.

9. The composition of claim 8, wherein said aqueous medium comprises a water soluble drug.

10. The composition of claim 9, wherein said drug is an anthelmintic.

11. The composition of claim 8, wherein the composition comprises about 7.5% w/v DEET.

12. The composition of claim 11, wherein the liposome is a cationic liposome.

13. The composition of claim 1, wherein the liposome is a neutral liposome.

14. The composition of claim 1, wherein the liposome is an anionic liposome.

15. The composition of claim 1, wherein the liposome comprises L-α-phosphatidylcholine, stearylamine and cholesterol.

16. An insect repellant and antiparasitic composition comprising a liposome and DEET, said liposome having a phospholipid-containing membrane entrapping an aqueous medium, wherein said DEET is interspersed with phospholipids of said membrane, and wherein said composition exhibits activity against insects and skin penetrating parasites for over 48 hours after application to the skin.

17. The composition of claim 16, wherein the liposome comprises a naturally occurring glycerophospholipid.

18. The composition of claim 16, wherein the liposome comprises a multilamellar liposome micelle.

19. The composition of claim 17, wherein the liposome comprises a multilamellar liposome micelle.

20. The composition of claim 19, wherein the composition comprises from about 1% w/v to about 50% w/v DEET.

21. The composition of claim 20, wherein the liposome comprises a naturally occurring glycerophospholipid.

22. The composition of claim 16, wherein the composition comprises from about 1% w/v to about 50% w/v DEET.

23. The composition of claim 16, wherein the composition comprises from about 7.0% w/v to about 10% w/v DEET.

24. The composition of claim 23, wherein said aqueous medium comprises a water soluble drug.

25. The composition of claim 23, wherein the composition comprises about 7.5% w/v DEET.

26. The composition of claim 16, wherein the liposome is a cationic liposome.

27. The composition of claim 16, wherein the liposome is a neutral liposome.

28. The composition of claim 16, wherein the liposome is an anionic liposome.

29. The composition of claim 16, wherein the liposome comprises L-α-phosphatidylcholine, stearylamine and cholesterol.

30. An insect repellant and antiparasitic composition comprising a liposome and DEET, said liposome having a phospholipid-containing membrane entrapping an aqueous medium, wherein said DEET is interspersed with phosphoipids of said membrane, and wherein said liposome comprises L-α-phosphatidyicholine, stearylamine and cholesterol.

31. The composition of claim 30, wherein the liposome comprises a multilamellar liposome micelle.

32. The composition of claim 30, wherein the composition comprises from about 1% w/v to about 50% w/v DEET.

33. The composition of claim 32, wherein the liposome comprises a multilamellar liposome micelle.

34. The composition of claim 30, wherein the composition comprises from about 7.0% w/v to about 10% w/v DEET.

35. The composition of claim 30, wherein said aqueous medium comprises a water soluble drug.

* * * * *